United States Patent
Maslowski et al.

(10) Patent No.: US 10,327,727 B2
(45) Date of Patent: Jun. 25, 2019

(54) AUTOMATIC ESTIMATING AND REDUCING SCATTERING IN COMPUTED TOMOGRAPHY SCANS

(71) Applicant: VARIAN MEDICAL SYSTEMS, INC., Palo Alto, CA (US)

(72) Inventors: Alexander E. Maslowski, Lexington, KY (US); Adam Wang, Menlo Park, CA (US); Josh Star-Lack, Palo Alto, CA (US); Mingshan Sun, Menlo Park, CA (US); Todd Wareing, Gig Harbor, WA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 211 days.

(21) Appl. No.: 15/593,342

(22) Filed: May 12, 2017

(65) Prior Publication Data
US 2018/0325485 A1  Nov. 15, 2018

(51) Int. Cl.
*A61B 6/00* (2006.01)
*A61B 6/03* (2006.01)
(Continued)

(52) U.S. Cl.
CPC ............ *A61B 6/5282* (2013.01); *A61B 6/032* (2013.01); *A61B 6/4035* (2013.01);
(Continued)

(58) Field of Classification Search
CPC ..... A61B 6/032; A61B 6/4035; A61B 6/4085; A61B 6/483; A61B 6/5282; G01N 23/046;
(Continued)

(56) References Cited

U.S. PATENT DOCUMENTS

| 2002/0106054 A1* | 8/2002 | Caflisch ................. A61N 5/103 378/65 |
| 2011/0164722 A1 | 7/2011 | Wiegert et al. |
| 2016/0213345 A1 | 7/2016 | Star-Lack et al. |

FOREIGN PATENT DOCUMENTS

| EP | 2009592 A2 | 12/2008 |
| EP | 2009592 A3 | 8/2011 |

OTHER PUBLICATIONS

The Extended European Search Report, Application No. 18170587.2, dated Oct. 12, 2018.
(Continued)

*Primary Examiner* — Manuchehr Rahmjoo
(74) *Attorney, Agent, or Firm* — Su IP Consulting

(57) ABSTRACT

In accordance with at least some embodiments of the present disclosure, a process to estimate scattered radiation contained in x-ray projections for computed tomography (CT) reconstruction is provided. The process may construct an object model based on a plurality of projection images generated by CT scanning of an object using an x-ray radiation source and a detector panel. The process may construct a virtual radiation source based on the x-ray radiation source, and a virtual detector panel based on the detector panel. The process may perform a simulated CT scanning of the object model by simulating macroscopic behavior of particles being emitted from the virtual radiation source, passing through the object model, and being detected by the virtual detector panel. And the process may generate a simulated scatter image based on a first subset of particles scattered during the simulated CT scanning of the object model.

19 Claims, 7 Drawing Sheets

(51) Int. Cl.
| | |
|---|---|
| G01N 23/046 | (2018.01) |
| G06T 5/00 | (2006.01) |
| G06T 11/00 | (2006.01) |
| G09B 23/28 | (2006.01) |
| G06T 7/00 | (2017.01) |
| G06T 11/20 | (2006.01) |
| G21K 1/10 | (2006.01) |
| G21K 5/04 | (2006.01) |

(52) U.S. Cl.
CPC ............ *A61B 6/4085* (2013.01); *A61B 6/483* (2013.01); *G01N 23/046* (2013.01); *G06T 5/00* (2013.01); *G06T 5/002* (2013.01); *G06T 7/0012* (2013.01); *G06T 11/005* (2013.01); *G06T 11/20* (2013.01); *G09B 23/286* (2013.01); *G06T 2207/10081* (2013.01); *G21K 1/10* (2013.01); *G21K 5/04* (2013.01)

(58) Field of Classification Search
CPC ................... G06T 11/005; G06T 11/20; G06T 2207/10081; G06T 5/00; G06T 5/002; G06T 7/0012; G09B 23/286; G21K 1/10; G21K 5/04
See application file for complete search history.

(56) References Cited

OTHER PUBLICATIONS

Mingshan Sun et al., "Rapid Scatter Estimation for CBCT using the Boltzmann Transport Equation", Proc. SPIE Medical Imaging, 2014.
Alexander Maslowski et al., "AcurosCTS: A Scatter Prediction Algorithm for Conebeam Tomography", ANS MC2015—Joint International Conference Mathematics and Computation (M &C), Supercomputing in Nuclear Application (SNA) and the Monte Carlo (MC) Method, Apr. 19-23, 2015.
A. Want et al., "TH-EF-BRA-02: Patient-Specific Dose Maps for CT Scans Using a Fast, Deterministic Boltzmann Transport Equation Solver", American Association of Physicists in Medicine, Jun. 2015, vol. 42, Issue 6.
M Sun et al., "Improved Scatter Correction Using Adaptive Scatter Kernel Superposition", Phys. Med. Biol., 2010, pp. 6695-6720, vol. 55, IOP Publishing.
M. J. Daly et al., "Intraoperative Cone-beam CT for Guidance of Head and Neck Surgery: Assessment of Dose and Image Quality Using a C-arm Prototype", Medical Physics, Oct. 2006, pp. 3767-3780, vol. 33, No. 10.
L. Alan Love et al., "Scatter Estimation for a Digital Radiographic System Using Convolution Filtering", Med. Phys., Mar./Apr. 1987, pp. 178-185, vol. 14, No. 2.
Steven F. Petit et al., "Calibration of Megavoltage Cone-beam CT for Radiotherapy Dose Calculations: Correction of Cupping Artifacts and Conversion of CT Numbers to Electron Density", Medical Physics, Mar. 2008, pp. 849-865, vol. 35, No. 3.
A. P. Colijn et al., "Accelerated Simulation of Cone Beam X-Ray Scatter Projections", IEEE Transactions on Medial Imaging, May 2004, pp. 584-590, vol. 23, No. 5.
Yiannis Kyriakou et al., "Combining Deterministic and Monte Carlo Calculations for Fast Estimation of Scatter Intensities in CT", Physics in Medicine and Biology, 2006, pp. 4567-4586, No. 51.
Wojciech Zbijewski et al., "Efficient Monte Carlo Based Scatter Artifact Reduction in Cone-Beam Micro-CT", IEEE Transactions on Medical Imaging, Jul. 2006, pp. 817-827, vol. 25, No. 7.
Michael Meyer et al., "A Fast and Pragmatic Approach for Scatter Correction in Flat-Detector CT Using Elliptic Modeling and Iterative Optimization", Physics in Medicine and Biology, 2010, pp. 99-120, vol. 55, IOP Publishing.
Oleg N Vassiliev et al., "Validation of a New Grid-based Boltzmann Equation Solver for Dose Calculation in Radiotherapy with Photon Beams", Physics in Medicine and Biology, 2010, pp. 581-598, vol. 55, IOP Publishing.
K. Bush et al., "Dosimetric Validation of Acuros XB with Monte Carlo Methods for photon Dose Calculations", Medical Physics, Apr. 2011, pp. 2208-2221, vol. 38, No. 4.
Kent A Gifford et al., "Comparison of a Finite-Element Multigroup Discrete-Ordinates Code with Monte Carlo for Radiotherapy Calculations", Physics in Medicine and Biology, 2006, pp. 2253-2265, vol. 51.
K. Zourari et al., "Dosimetric Accuracy of a Deterministic Radiation Transport Based 192Ir Brachytherapy Treatmeni Planning System. Part I: Single Sources and Bounded Homogeneous Geometries", Medical Physics, Feb. 2010, pp. 649-661, vol. 37, No. 2.
L. Petrokokkinos et al., "Dosimetric Accuracy of a Deterministic Radiation Transport Based 192Ir Brachytherapy Treatment Planning System. Part II: Monte Carlo and Experimental Verification of a Multiple Source Dwell Position Plan Employing a Shielded Applicator", Medical Physics, Apr. 2011, pp. 1981-1992, vol. 38, No. 4.
Todd A. Wareing et al., "A First Collison Source Meeting for Attila, an Unstructured Tetraheadral Mesh Discrete Ordinates Code", Topical Meeting on Radiation Protection and Shielding, Apr. 19-23, 1998.

\* cited by examiner

Boltzmann Transport Equation
(510)

AUTOMATIC ESTIMATING AND REDUCING SCATTERING IN COMPUTED TOMOGRAPHY SCANS

BACKGROUND OF THE DISCLOSURE

Embodiments of the present disclosure relate generally to rapid, accurate and fully automated system and method to estimate and reduce scatter artifacts in computed tomography scans.

DESCRIPTION OF THE RELATED ART

Unless otherwise indicated herein, the approaches described in this section are not prior art to the claims in this application and are not admitted to be prior art by inclusion in this section.

Scattering remains one of the main challenges for cone-beam Computed Tomography (CBCT) image quality due to the nature of wide-area beam emitted from an x-ray radiation source. The CBCT scatter-to-primary ratio (SPR) often exceeds 1 even with scatter-reduction measures such as a bowtie filter and anti-scatter grid in place. In spite of these scatter-reduction measures, scatter signal, including due to the patient and patient table, is particularly hard to reduce. Other scatter estimation and correction methods, which are based on Monte Carlo calculation, may stochastically track particles through the object and the components of the imaging system. However, Monte Carlo calculations are typically slow, resource intensive, and generate noisy results.

DETAILED DESCRIPTION

Figure 1:
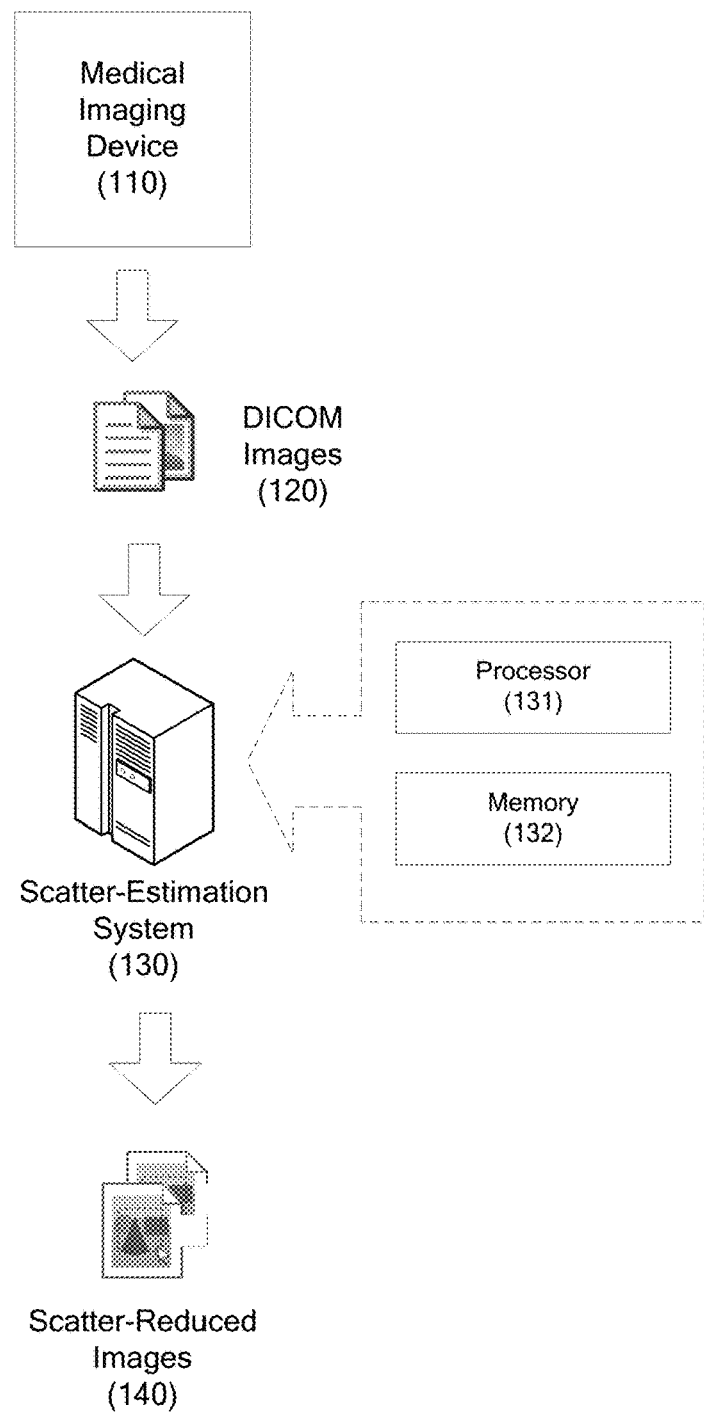
FIG. 1 shows a block diagram illustrating an exemplary system configured to estimate and reduce scatter artifacts in CT scan images.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated herein.

FIG. 1 shows a block diagram illustrating an exemplary system configured to estimate and reduce scatter artifacts in CT scan images, in according to certain embodiments of the present disclosure. In FIG. 1, a medical imaging device 110 may perform a CT scan operation on a patient, and generate a set of Digital Imaging and Communications in Medicine (DICOM) images 120 which may contain scatter artifacts. A scatter-estimation system 130 may take the DICOM images 120 as inputs, and generate a set of scatter-reduced images 140 that have reduced scatter artifacts. The scatter-reduced images 140 may be used to generate better-quality CT volumes for diagnostic purposes.

Examples of the medical imaging device 110 may include, without limitation, X-ray device, CT device, cone-beam CT (CBCT) device, and others. The medical imaging device 110 may have a "radiation source" for emitting cone-beam, pencil-beam, and/or fan-beam particles (e.g., photons and/or electrons). The medical imaging device 110 may have a "detector panel" for detecting particles emitted from the radiation source and passed through a "CT scanning object" (e.g., a patient) placed between the radiation source and the detector panel. The emitted particles may be generated inside a spectrum ranging from 0 keV to 150 keV, and may interact with the scanning object through photoelectric absorptions, Rayleigh (or coherent) scattering, and Compton (or incoherent) scattering. The present disclosure evaluates the radiation effect of particles that can reach the detector panel of the medical imaging device 110.

During one CT scanning interrogation, the medical imaging device 110 may project particles towards the detector panel at a particular angle/direction, and generate a DICOM image 120, or projection, based on the particles detected by the detector panel. Afterward, the radiation source-detector panel (source-detector pair) may be rotated to a different angle/direction, in order to perform another round of CT scanning interrogation of the scanning object and generate another DICOM image 120. Throughout the disclosure, the terms "image", "projection", "projection image", and "DICOM image" are used interchangeably to broadly refer to 2-dimension (2D) medical data generated from a single CT scanning interrogation. Thus, a "CT scanning operation" may include multiple CT scanning interrogations from multiple angles/directions, and may generate a set of corresponding DICOM images 120.

In some embodiments, the scatter-estimation system 130 may provide an interface to allow a user uploading a patient's DICOM images 120 obtained from a CT scanning operation. The scatter-estimation system 130 may process the DICOM images 120, and generate a set of scatter images each of which containing an estimation of the scatter artifacts in the DICOM images 120. The scatter-estimation system 130 may further utilize the scatter images for reducing the scatter artifacts in the DICOM images 120, as well as generating a set of scatter-reduced images 140.

In some embodiments, the scatter-estimation system 130 may include one or more processors 131, memory 132, and/or other components, so that it could process the DICOM images 120 and generate the scatter-reduced images 140. In some embodiments, the processor(s) 131 may include central processing units (CPUs) for controlling the overall operation of the scatter-estimation system 130. The processor(s) 131 may accomplish this by executing software or firmware stored in memory 132. The processor(s) 131 may be or may include, one or more programmable general-purpose or special-purpose microprocessors, digital signal processors (DSPs), programmable controllers, application specific integrated circuits (ASICs), programmable logic devices (PLDs), graphical processing units (GPUs) or the like, or a combination of such devices. The memory 132 may represent any form of random access memory (RAM), read-only memory (ROM), flash memory (as discussed above), or the like, or a combination of such devices. In use, the memory 132 may contain, among other things, a set of machine readable instructions which, when executed by the processor 131, causing the processor 131 to perform at least some embodiments of the present disclosure.

Figure 2:
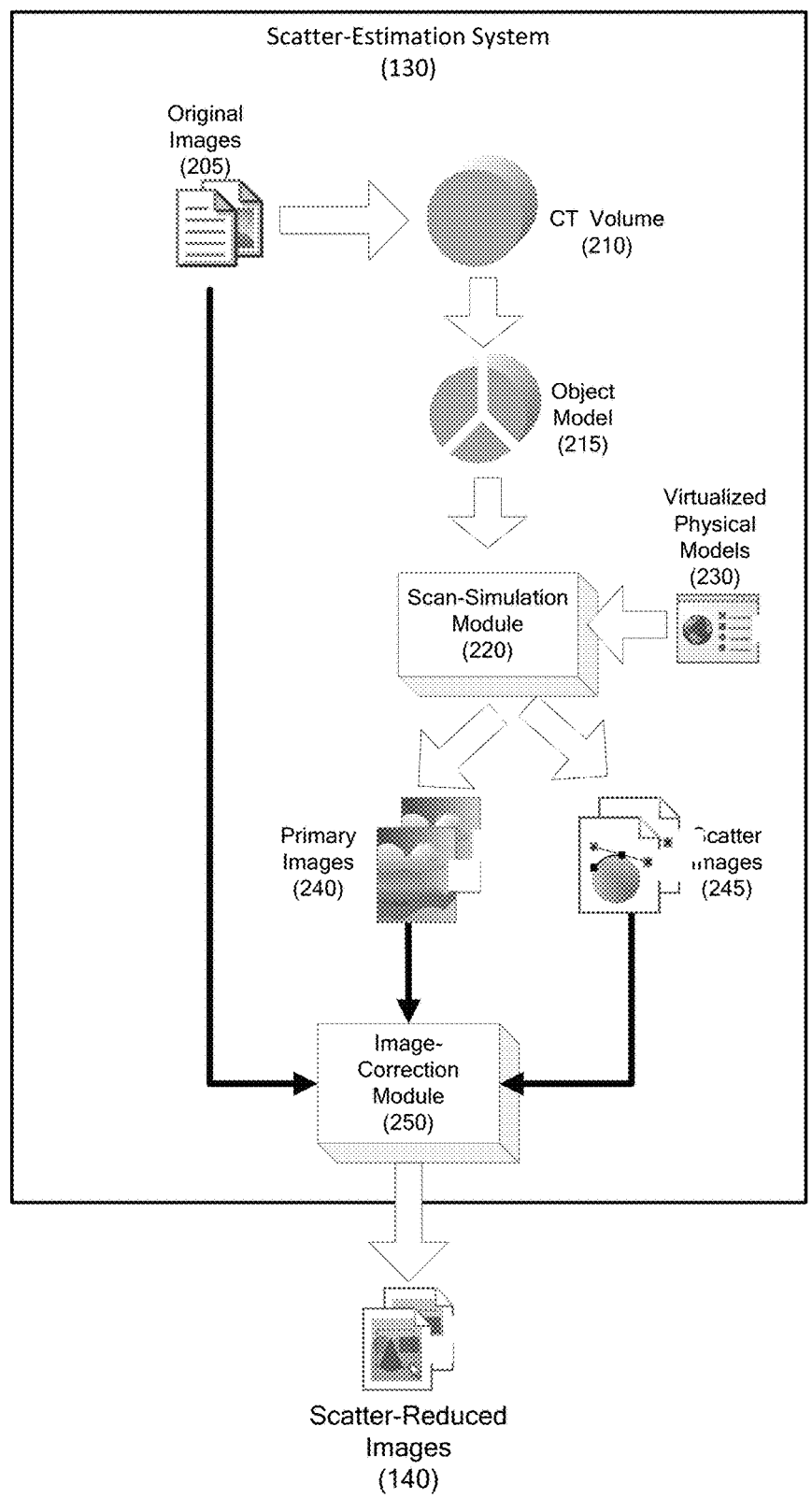
FIG. 2 illustrates an exemplary scatter-estimation system for estimating and reducing scatter artifacts in CT projection images.

FIG. 2 illustrates an exemplary scatter-estimation system for estimating and reducing scatter artifacts in CT projection images, in accordance with certain embodiments of the present disclosure. In FIG. 2, the scatter-estimation system 130 may be configured to simulate a CT scanning operation against an object model 215, and estimate the scattering effect during the simulated CT scanning operation. The scatter-estimation system 130 may contain, among other elements, a scan-simulation module 220 and an image-correction module 250. The modules contained in the scatter-estimation system 130 may be implemented either as hardware components or software applications running on a suitable computer. Further, some of the above modules may be combined into a single module, or a single module may be divided into additional sub-modules not shown in FIG. 2.

In some embodiments, the scatter-estimation system 130 may perform a first-pass reconstruction operation to convert a set of original images 205 (e.g., DICOM images 120 of FIG. 1) into a CT volume 210. The CT volume 210 may be used to show in 3-dimension (3D) the distribution of materials inside the scanning object. Throughout the disclosure, the terms "volume", "3D volume", and "CT volume" may be used interchangeably to broadly refer to 3D medical data reconstructed based on a set of DICOM images. For example, a 3D CT volume of a patient's heart may be reconstructed based on a set of 2D DICOM images or 2D projections taken by a CT scanner through the patient's heart and its surrounding anatomy.

In some embodiments, the scatter-estimation system 130 may further construct one or more object models 215 based on the CT volume 210. Since the CT volume 210 is generated based on a specific scanning object (e.g., a patient), the object model 215 may be used to model and simulate the patient's anatomical parts such as breasts, lungs, heart, stomach, liver, pancreas, spleen, kidneys, colon, small intestine, bladder, gonads, uterus/cervix (female), prostate (male), skeletal bone, bone marrow, and skin, etc. Further, the scan-simulation module 220 may be configured to perform a simulated CT scanning operation on the object model 215, in order to estimate/predict the scattering effects that may occur during the actual CT scanning operation performed on the scanning object.

In some embodiments, the scan-simulation module 220 may be configured to simulate a CT scanning operation on the object model 215 and generate a set of simulated CT images (e.g., primary images 240 and scatter images 245). Specifically, the scan-simulation module 220 may construct a "virtual scanning environment" based on a set of virtualized physical models 230. The virtualized physical models 230 may be configured to mimic/simulate a "physical scanning environment" utilized by the actual CT scanning operation. For example, the physical scanning environment may include, without limitation, an x-ray beam, a detector panel, a collimator, a bow-tie filter, an anti-scatter grid, and a patient table. Likewise, the virtual scanning environment may include, without limitation, a virtual x-ray beam, a virtual detector panel, a virtual collimator, a virtual filter, a virtual anti-scatter grid, and a virtual patient table, all of which correspond to their respective physical counter-parts in the physical scanning environment.

In some embodiments, after constructed the object model 215 and the virtual scanning environment, the scan-simulation module 220 may simulate macroscopic behavior of x-ray particles endeavoring on traveling paths that include being emitted from the virtual x-ray beam, passing through the object model 215, and being detected by the virtual detector panel. Optionally, the scan-simulation module 220 may simulate the x-ray particles passing through the virtual collimator, the virtual filter, and/or the virtual anti-scatter grid during the above traveling paths.

In some embodiments, the scan-simulation module 220 may estimate those x-ray particles that were not scattered before being detected by the virtual detector panel, and generate a simulated image (primary image 240) based on these un-scattered particles. Likewise, the scan-simulation module 220 may generate another simulated image (scatter image 245) based on particles that are scattered at least once during the above simulated traveling paths. In other words, the primary image 240, which contains estimated information that are not affected by scattering, may be used to ascertain the useful information in the original images 205, and the scatter image 245, which contains estimated information that are affected by scattering, may be used to evaluate the scatter artifacts in the original images 205.

In some embodiments, similar to multiple CT scanning interrogations in one CT scanning operation, the scan-simulation module 220 may simulate the rotating of virtual radiation source and virtual detector panel to different angles/directions, and perform multiple rounds of simulated CT scanning interrogation against the object model 215. During each simulated CT scanning interrogation, the scan-simulation module 220 may generate a corresponding primary image 240 and a corresponding scatter image 245. After completed all simulated CT scanning interrogations in a simulated CT scanning operation, the scatter-estimation system 130 may transmit the primary images 240 and the scatter images 245 to the image-correction module 250 for further processing.

In some embodiments, the image-correction module 250 may be configured to estimate a set of scatter-reduced images 140 by processing the original images 205 using the scatter images 245. A "scatter-reduced" image may refer to an original image 205 that has its scatter artifacts reduced/eliminated with the help of a scatter image 245. Specifically, the image-correction module 250 may generate the scatter-reduced images 140 by adjusting the original images 205 using subtraction or perturbation based on the scatter image 245. In other words, the image-correction module 250 may subtract a scatter image 245 from an original image 205, or perform a perturbation operation on an original image 205 using a scatter image 245. The resulting scatter-reduced images 140 may be used for reconstructing a CT volume with reduced scatter artifacts in comparison to the CT volume 210.

Figure 3:
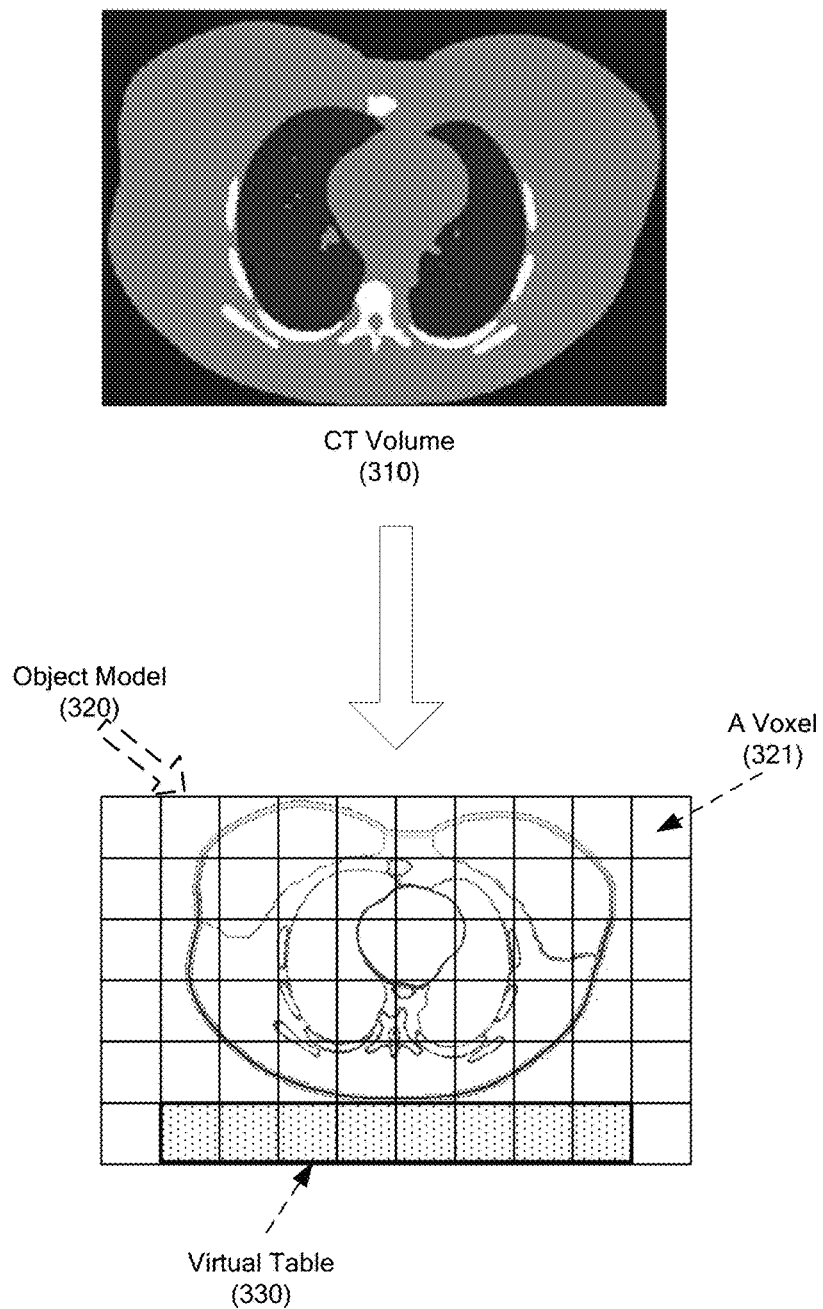
FIG. 3 illustrates a scenario to construct an object model based on a CT volume.

FIG. 3 illustrates a scenario to construct an object model based on a CT volume, according to certain embodiments of the present disclosure. In FIG. 3, a scatter-estimation system (similar to the scatter-estimation 130 of FIG. 2) may first perform a first-pass reconstruction to generate a CT volume 310 based on a set of original images. Afterward, the scatter-estimation system may create an object model 320 corresponding to the CT volume 310.

In some embodiments, the "CT volume" or the "object model" may contain a set of 3D cells (or "voxels"). A voxel (e.g., voxel 321) represents a value on a fixed and regular grid in 3D space, and may correspond to one of the multiple 3D structures, such as, without limitation, cubes, rectangular cuboids, hexagonal structures (e.g., structures having two hexagons as bases and six rectangular sides, with the lengths of all edges being identical), or structures in any isotropic/non-isotropic shapes and sizes (e.g., 1 cm). When constructing an object model 320 based on a CT volume 310, the scatter-estimation system may specify the object model 320's dimensions, voxel size, and location of the center.

In some embodiments, the scatter-estimation system may configure the object model 320 having the same or different voxel-sizes in view of the voxels in the CT volume 310. For example, the scatter-estimation system may discretize the CT volume 310 into two voxel sizes, one with smaller isotropic voxels (e.g., 1.25 mm) and another with larger isotropic voxels (e.g., 12.5 mm). Afterward, the scatter-estimation system may utilize the smaller isotropic voxels to generate primary images, and utilize the larger isotropic voxels to estimate scatter images. Configuring the voxels of the object model 320 to be larger than voxels in the CT volume 310 may be referred to as down-sampling. In other words, down-sampling may allow the object model 320 to have fewer voxels (e.g., 46×46×25 voxels) than the CT volume 310, thereby increasing the speed of the estimating of the scatter images.

In some embodiments, each of the voxels in the CT volume 310 may contain Hounsfield Units (HU) values derived from the original images. The scatter-estimation system may assign a corresponding HU value for each of the voxels in the object model 320 based on the HU value of the corresponding voxel in the CT volume 310. In down-sampling situation, a single voxel in the object model 320 may be associated with multiple voxels in the CT volume 310. In this case, the scatter-estimation system may calculate an average of the HU values obtained from these multiple voxels, and assign this average HU value to the single voxel in the object model 320.

In some embodiments, the scatter-estimation system may further assign a specific material type and density value for each of the voxels in the object model 320, based on the HU value of the voxels. A voxel's material type and density value may determine the voxel's x-ray attenuation and scattering properties. Exemplary material types may include, without limitation, water, bone, adipose, lung, muscle, cartilage, aluminum, titanium. A voxel's density value may then be determined based on the voxel's material type, in according to this material type's physical characteristics.

In some embodiments, the scatter-estimation system may assign a voxel's material type based on a linear-combination of multiple materials types. The scatter-estimation system may evaluate the HU gradient of the voxels in the object model 320, and identify structures in the CT volume 210 that have distinctive features using previously-defined HU value thresholds and density ranges. Each identified structure may then be classified, based on its respective HU values, to either non-organ materials (such as air, water), or organ regions (such as lung, adipose, soft-tissue, muscle or bone). Alternatively, the scatter-estimation system may support two or more material types and density values per voxel. For HU value that is less than a certain threshold, e.g., 100 mHU, the scatter-estimation system may assign a zero density value to the voxel, in order to simplify subsequent processing.

In some embodiments, the scatter-estimation system may extend the object model 320 in the superior-inferior direction since some particles may scatter into these regions and back into the scanning object and/or the detecting panel during a CT scanning operation. In other words, the CT volume 310 may be truncated in the superior-inferior direction, and the scatter-estimation system may extend the object model 320 in the top and bottom positions uniformly to create additional volume of voxels, in order to capture scattering in this superior-inferior direction.

In some embodiments, a patient table used to support the scanning object may be a substantial source of scattering in an actual CT scanning operation, particularly during lateral-view CT scanning interrogations. In this case, the scatter-estimation system may extend the field-of-view (FOV) of the CT volume 310 during its first-pass reconstruction, in order to ensure that the patient table may be encompassed within the FOV. Thus, although the patient table may often be truncated in the original images, the scatter-estimation system may at least partially extend/reconstruct the truncated patient table in the reconstructed CT volume 310.

In some embodiments, the scatter-estimation system may encompass/simulate a virtual table 330 in the object model 320 to account for scattering caused by a patient table. Specifically, the scatter-estimation system may model the virtual table 330 based on prior knowledge, such as CAD models or pre-scans of the patient table. For example, the scatter-estimation system may configure the virtual table 330 with known table types, spatial constraints (e.g., height, lateral, longitudinal positions), and configurations (e.g., sliding rails beneath the table). The prior knowledge may be provided in XML files that describe points along the surface of the components (table exterior/interior, left/right rail, top/bottom/sides) in the axial plane. Anything in the object model 320 below the top of the table surface may be replaced by the virtual table 330. The material type for the table components may be set as water.

Figure 4:
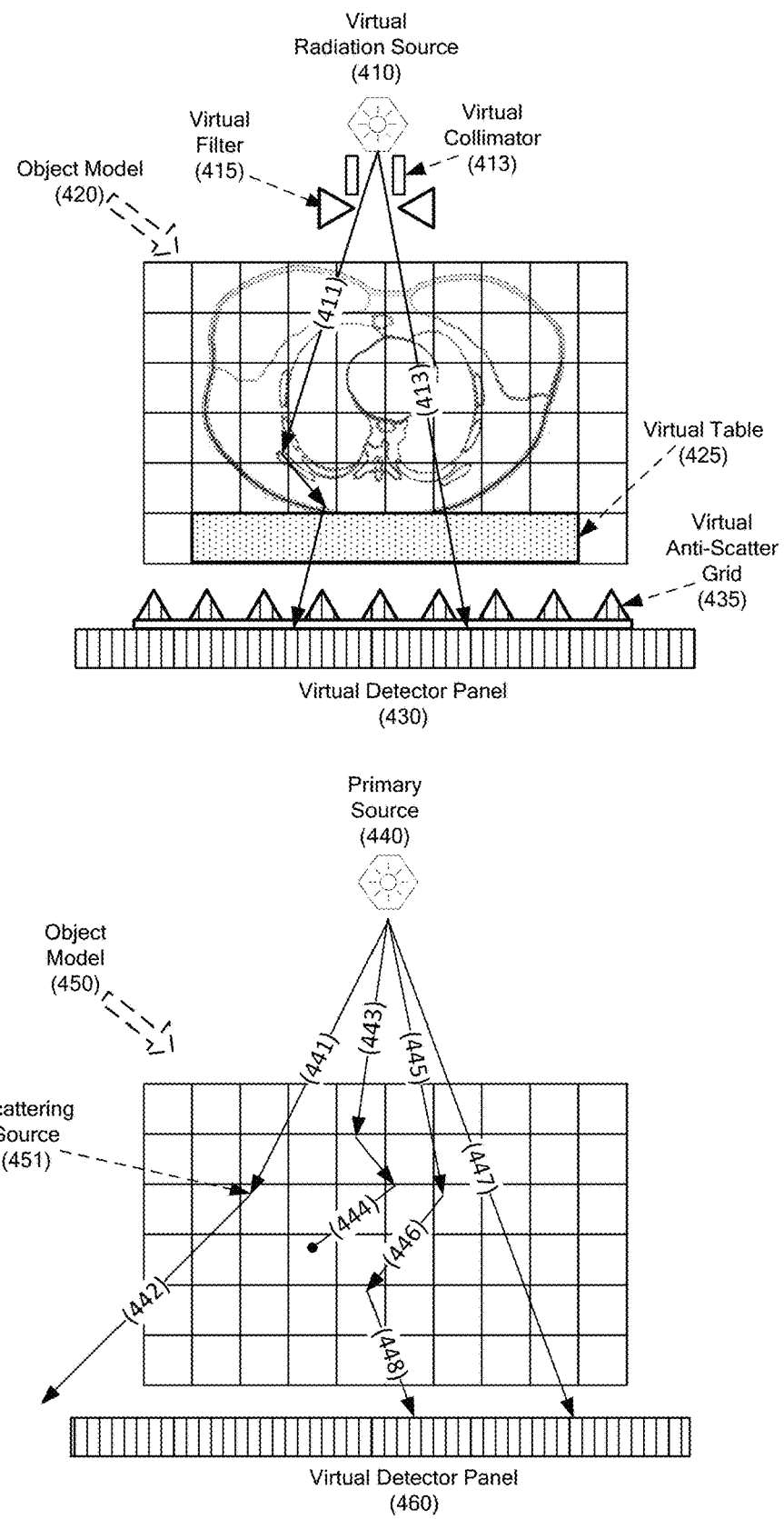
FIG. 4 illustrates a simulated clinical CT scanning operation.

FIG. 4 illustrates a simulated clinical CT scanning operation, in accordance with certain embodiments of the present disclosure. Assuming the object model 420 is constructed based on projection images generated by a CT scanner having a radiation source (e.g., x-ray beam) and a detector panel, a scan-simulation module (e.g., the scan-simulation module 240 of FIG. 2) may be configured to simulate such CT scanner performing a similar CT scanning operation on the object model 420. Specifically, the scan-simulation module may construct a virtual radiation source 410 and a virtual detector panel 430, and perform a simulated CT scanning of the object model 420 by simulating macroscopic behaviour of particles ("virtual beam") being emitted from the virtual radiation source 410, passing through the object model 420, and being detected by the virtual detector panel 430. The scan-simulation module may simulate additional virtualized physical models such as virtual collimator 413, virtual filter 415, and/or virtual anti-scatter grid 435.

In some embodiments, the scan-simulation module may simulate a virtual beam that describes (in energy, streaming direction and space) how x-ray particles travel from the virtual radiation source 410 through the virtual collimator 413 and the virtual filter 415 into the object model 420. The virtual beam may account for radiation source voltage, collimation, filtration, heel effect, and/or penumbra during the ray-tracing of the x-ray particles. For example, the virtual beam may include the effects of the virtual filter 415, account for secondary radiation sources such as off-focal radiation and scattering from virtual filter 415, allow the expansion of the virtual radiation source 410 beyond the virtual detector panel 430, and/or adjust collimation by the virtual collimator 413 to capture the penumbra.

In some embodiments, the scan-simulation module may model the virtual radiation source 410 as an x-ray point-source located at a specified distance from the isocenter (e.g., 100 cm) of the simulated CT scanning operation. The spectrum of the virtual beam from the virtual radiation source 410 may be discretized into energy groups (i.e., bins), and the scan-simulation module may model the virtual beam with various beam intensities. Further, the scan-simulation module may direct each energy group of the virtual beam (e.g., via travel paths 411 and 413) toward the virtual detector panel 430. In some embodiments, the scan-simulation module may model the virtual radiation source 410 based on an actual CT scanner's configuration parameters, such as Scanner Model, kV, Exposure, Scan Range, Longitudinal Coverage, Helical Pitch, Scan Start/Stop Angle, Noise Index, Source Filtration, Bowtie Filter, CTDIvol, DLP, etc.

In some embodiments, the scan-simulation module may model a virtual collimator 413 based on a physical collimator used during an actual CT scanning operation. For example, the virtual collimator 413 may have a configured collimation blade margin of 8 mm on all sides to ensure that penumbra caused by the particles from the virtual radiation source 410 is outside of the image generated by the virtual detector panel 430. The scan-simulation module may utilize the virtual collimator 413 to simulate the extra scattering that may be caused by the physical collimator.

In some embodiments, the scan-simulation module may model a virtual filter 415 based on a physical bow-tie filter used during an actual CT scanning operation. The scan-simulation module may also model the virtual filter 415 using images acquired with and without the bow-tie filter. Specifically, the scan-simulation module may estimate the equivalent aluminum thickness of the bow-tie filter ("bow-tie thickness"), and attenuate the virtual beam based on the estimated bow-tie thickness. In addition, the edges of the estimated bowtie thickness may be uniformly extended in all directions.

In some embodiments, the scan-simulation module may model a virtual anti-scatter grid 435 based on a physical anti-scatter grid used during an actual CT scanning operation. Specifically, the scan-simulation module may configure an anti-scatter grid function for the virtual anti-scatter grid 435 to simulate how the anti-scatter grid 435 filter behaves with respect to the scattered and un-scattered particles. The anti-scatter grid function may depend on the incident angles of the scattered particles, the incident angles of the un-scattered particles, and the energy of the scattered particles. Further, the anti-scatter grid function may depend on the relative thickness of the lamella that shields the pixels of the virtual detector panel 430 from the scattered particles. The anti-scatter grid function may also be implemented based on multiple models of anti-scatter grid hardware.

In some embodiments, the scan-simulation module may model a virtual detector panel 430 based on a physical detector panel used during an actual CT scanning operation. Specifically, the scan-simulation module may configure a detector response function for the virtual detector panel 430 to simulate how the virtual detector panel 430 captures x-ray particles. The detector response function may depend on the energy as well as the incident angles of the particles. The detector response function may compute the energy imparted by either scattered particles or un-scattered particles. The detector response function may also be implemented based on multiple models of detector panel hardware.

In some embodiments, the scan-simulation module may model the virtual detector panel 430 with multiple virtual pixels forming a grid. For example, the virtual detector panel 430 may have 75×100 number of virtual pixels, with each pixel being 4 mm×4 mm in size. The scan-simulation module may estimate the energy deposited in each of the virtual pixels, and utilize the deposited energy to generate an estimated image (e.g., primary image or scatter image).

As shown by the top-half of FIG. 4, after configured a virtual scanning environment including the virtual radiation source 410 and the virtual detector panel 430, and optionally including the virtual collimator 413, the virtual filter 415, and/or the virtual anti-scatter grid 435, the scan-simulation module 240 may perform a simulated CT scanning operation by simulating particles emitting from the virtual radiation source 410 along a source trajectory, and passing through the object model 420 via travel paths 411 and 413 before reaching the virtual detector panel 430.

As shown by the bottom-half of the FIG. 4, the scan-simulation module may simulate a beam of particles emitting from the virtual radiation source 440 (primary source) and passing through the virtual model 450 via traveling paths 441, 443, 445, and 447. This beam of particles from the primary source may be referred to as a "primary beam." During the first iteration of simulation, the scan-simulation module may ray-trace the primary beam's traveling paths, and simulate the particles of the primary beam passing, being scattered, or being absorbed among the voxels of the object model 450. In FIG. 4's example, a particle indicated by traveling path 441 may scatter in one of the voxels in the object model 450. The scan-simulation module may treat the location of the scattering as a scattering source 451, from which the particle embarks on a new traveling path 442 at the same or lower energy. During the first iteration of simulation, the scan-simulation module may collect all the scattering sources instigated by particles from the primary beam, and consider these scattering sources as "first iteration scattering sources."

In a second iteration of simulation, the scan-simulation module may simulate the transporting of the particles from the first iteration scattering sources to nearby voxels. Some of the particles may pass through or be absorbed by the nearby voxels (as shown by travel path 444), while other particles may scatter to other directions (as shown by travel path 446), thereby creating new scattering sources (second iteration scatter sources). In a subsequent iteration of simulation, the scan-simulation module may simulate the particles traveling from the second iteration scattering sources to nearby voxels, and update the scattering sources for the next iteration. The scan-simulation module may perform additional iterations of the above simulation operations until convergence (arriving at a solution that is close to the exact solution within some pre-specified error tolerance, e.g., 0.001%), in order to estimate those particles that are scattered and those un-scattered during an actual CT scanning operation.

In some embodiments, during the above multiple iterations of simulation, the scan-simulation module may monitor those particles that are affected or not affected during the ray-tracing of the particles. Specifically, the scan-simulation module may deem those particles that are uninterrupted (un-scattered and un-absorbed) before reaching the virtual detector panel 460 (as shown by travel path 447) "un-scattered particles." In comparison, the scan-simulation module may treat those particles, which may have at least one scattering event before reaching the virtual detector panel, "scattered particles." Any other particles either absorbed or not eventually reached the virtual detector panel 460 may be disregarded.

In some embodiments, the scan-simulation module may examine the angular profiles and the energy magnitudes of these scattered and un-scattered particles. The angular profiles and the energy magnitudes of the virtual radiation source 410, which is configured by the scan-simulation module, may be used to determine the behaviours of the particles emitting from the primary source 440. Likewise, how the particles may be scattered or absorbed in the voxels, as well as how the voxels may affect the energies and behaviours of the particles, may be dictated by the material types and density values defined in each voxel of the object model 450. The scan-simulation module may then translate the attenuating and scattering properties of the particles into appropriate interaction coefficients (corresponding to Rayleigh scattering, photoelectric absorption, Compton scattering, etc.).

In some embodiments, the scan-simulation module may utilize a Boltzmann Transport Equation (BTE), which is capable of describing the macroscopic behaviours of the particles (e.g., photons with certain angular profiles and energy magnitudes) flowing through an object (e.g., voxels having certain material types and densities), to follow the above multiple iterations of estimations. The scan-simulation module may ray-trace the particles, which may be attenuated and scattered based on the material type and mass density composition of each voxel in the object model, toward the virtual detector panel 460. The scan-simulation module may then solve the BTE to provide a solution for estimating those particles that are scattered or un-scattered when traveling through the object model 450 before reaching the virtual detector panel 460.

Figure 5:
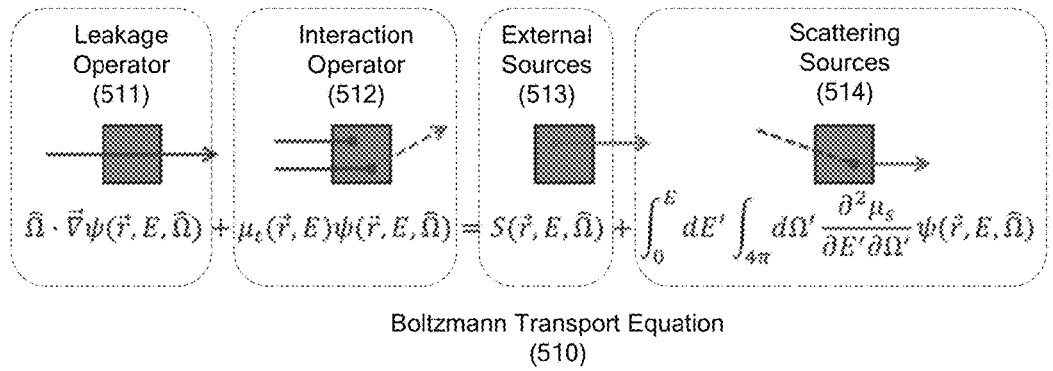
FIG. 5 illustrates using BTE to estimate scattered and un-scattered particles during a simulated CT scanning operation in order to generate a primary image and a scatter image.
Figure 5:
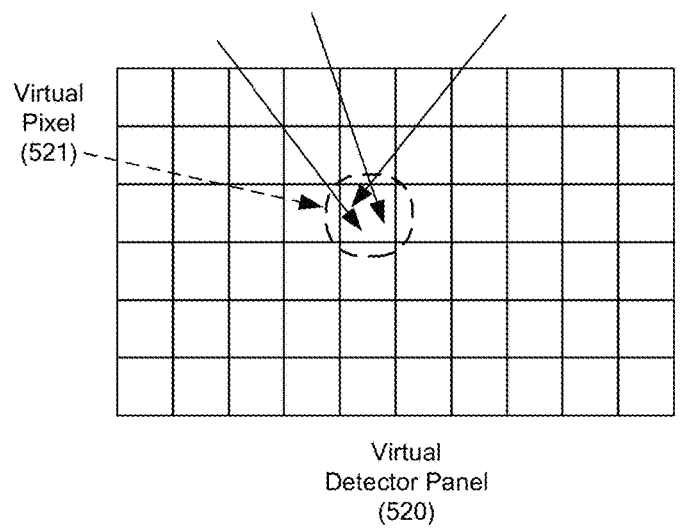

FIG. 5 illustrates using BTE to estimate scattered and un-scattered particles during a simulated CT scanning operation in order to generate a primary image and a scatter image, in accordance with certain embodiments of the present disclosure. In some embodiments, the scan-simulation module (similar to the scan-simulation module 240 of FIG. 2) may utilize a BTE 510 to record the above multiple iterations of simulation. The BTE 510 is a differential equation that governs the primary and scattering behaviours of particles, and can be numerically solved by discretizing phase-space (spatial location, energy, and/or angle) and applying a deterministic finite element algorithm. The discretization in space may be done using finite elements, the discretization in energy may be done using energy groups, and the discretization in angle may be done using discrete ordinates. The solution of the BTE 510 may be used to show the distribution of particle fluence across the voxels of the object model.

In FIG. 5, the BTE 510 has two items on the left of its equation: leakage operator 511 and interaction operator 512; and two items on the right of its equation: external sources 513 and scattering sources 514. In other words, the sum of the leakage operator 511 and interaction operator 512 equals to the sum of the external sources 513 and scattering sources 514. The leakage operator 511 defines the net particle out-flow from the volume; the interaction operator 512 defines the rate of particles interacting with media, such as by absorption or scattering; the external sources 513 define the sum of the particles from non-scattering sources, such as the x-ray source; and the scattering sources 514 define the particles scattering into the phase space.

With respect to the mathematic equation in the BTE 510, the variable r denotes a particle's spatial coordinates, the variable E denotes a particle's energy, and the variable $\Omega$ denotes a particle's streaming direction. Further, $\mu_t$ denotes the linear attenuation coefficient (which describes how easily a voxel can be penetrated by the particles), S denotes an external source of particles, and $\psi$ defines the particle fluence (or angular flux) described over spatial coordinates r, energy E and streaming direction $\Omega$. In other words, the "particle fluence" or "angular flux" is the sum of particle track lengths per unit volume and unit time in direction $\Omega$ at point r. Combined with known quantities such as the linear attenuation coefficient (the probability that a particle will interact per unit track length) or kerma (the energy released by particles interacting with the object), the particle fluence may be used to derive physically-measurable quantities such as particle energies (e.g., kV energies).

In some embodiments, the scan-simulation module may generate a primary image by ray-tracing those simulated un-scattered particles detected by the virtual pixels of the virtual detector panel. The scan-simulation module may also predict the scatter image based on the scattered particles reached the virtual pixels of the virtual detector panel. Specifically, the scan-simulation module may model the imaging capability of the virtual detector panel's virtual pixels, in order to generate the primary image and scatter image based on these kV energies estimated at each of the virtual pixels in the virtual detector panel.

In some embodiments, the scan-simulation module may initiate a BTE solver to perform the ray-tracing of particles from the primary source into the object model and scattering particles inside the object model in multiple iterations, before ray-tracing scattered particles from the object model to the virtual detector panel. The scan-simulation model may then calculate the scatter image by ray-tracing and summing up the scatter angular flux contribution from those voxels of the object model that have scattered particles passing through before reaching the virtual pixels in the virtual detector panel 520.

For example, the scan-simulation module 240 may record the scattered or un-scattered particles reaching the virtual pixel 521 during simulation. The scan-simulation module 240 may then apply those particles' macroscopic behaviour values to the respective coordination variable r, energy variable E, and directional variable $\Omega$ in the BTE 510. After inputting all relevant information into the BTE 510, the scan-simulation module may solve the BTE 510 by generating the solution $\psi$, which shows distribution of the particle fluence among all the virtual voxels. The particle fluence distributions among all the virtual voxels may then be ray-traced onto the virtual pixels of the virtual detector panel, which may then be used to generate a primary image or a scatter image. In other words, those virtual voxels that have the un-scattered or scattered particles passing through before reaching the virtual pixels of the virtual detector panel may have their corresponding particle fluence distribution values used to generate the primary image or the scatter image, respectively.

In some embodiments, the scan-simulation module 240 may utilize a "Monte Carlo method" solver or a "deterministic method" solver to calculate the particle fluence solution to the BTE 510. Monte Carlo method solver may converge to the solution by increasing the number of particles simulated (stochastic convergence), while the deterministic method solver may converge to the solution by refining the angular, spatial or energy mesh resolution (deterministic convergence). The deterministic method solver can be implemented using parallel algorithms, making it well-suited for general-purpose graphics processing units. Thus, the scan-simulation module may select the deterministic method solvers for solving the BTE 510 for its advances in computational efficiency and in allowing rapid and accurate dose calculations on desktop computers.

In some embodiments, the scan-simulation module may refine the discretized variables or adjust the parameters of the BTE solver, in order to optimize the BTE solver's accuracy and minimize its run times. For example, the BTE solver parameters that can be optimized include voxel size, energy grouping scheme, angular discretization, and scattering source representation. These parameters may be further adjusted to account for commercial CT scanner's trajectories, the source spectrum (including heel effect), variable collimation, bowtie filtration, and tube current modulation.

Referring back to FIG. 2, based on the primary images 240 and the scatter images 245 generated by the scan-simulation module 240, the image-correction module 250 may be configured to generate one or more scatter-reduced image 140, which may be used to generate another CT volume with reduced scatter artifacts in comparison to the CT volume 210.

Figure 6:
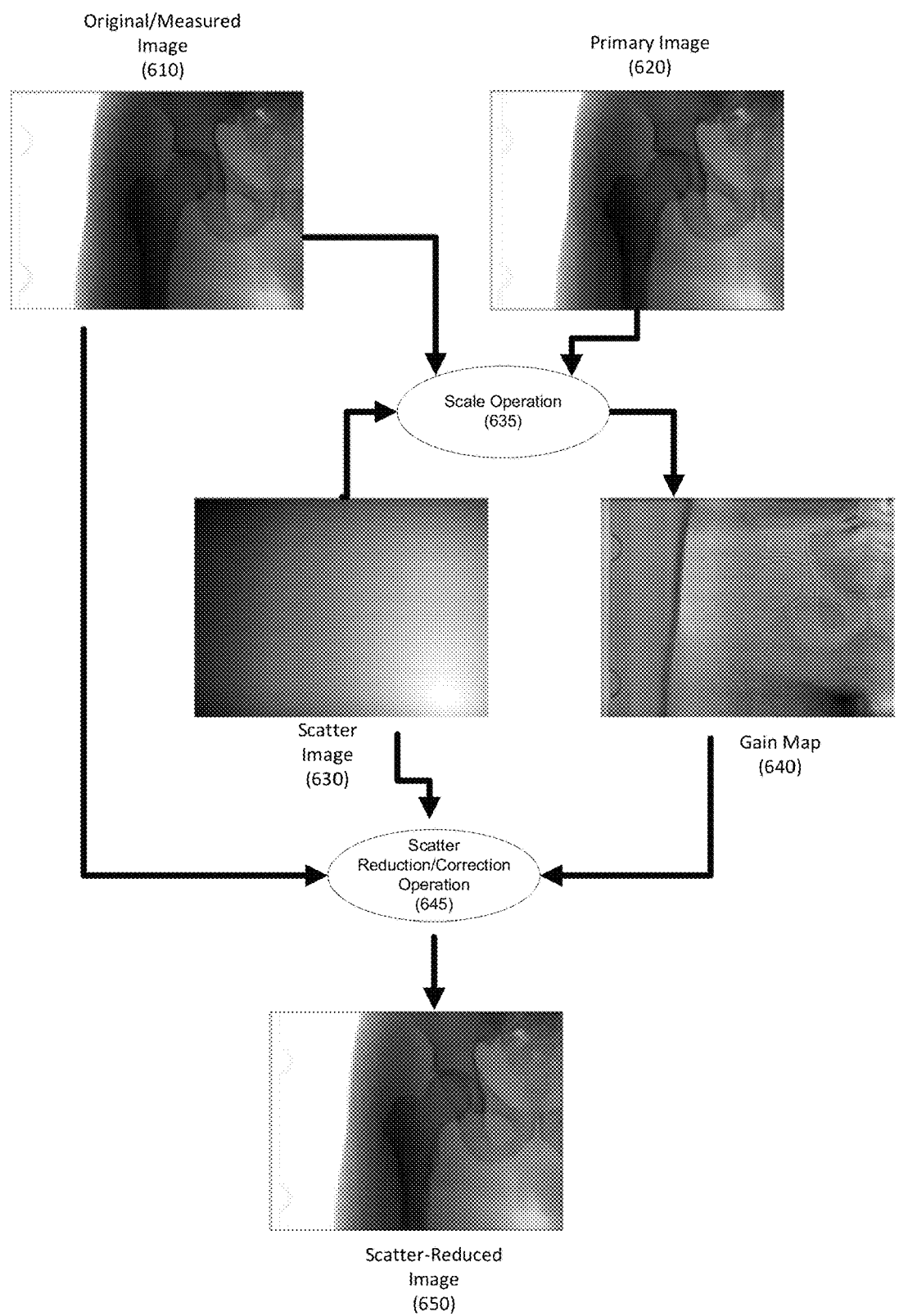
FIG. 6 illustrates an exemplary approach to generate a scatter-reduced image.

FIG. 6 illustrates an exemplary approach to generate a scatter-reduced image, in accordance with certain embodiments of the present disclosure. In FIG. 6, the original image 610 may be a DICOM image measured/generated by a CT scanner during an actual CT scanning operation, and may contain artifacts caused by scattering x-ray particles. A scan-simulation module of a scatter-estimation system (similar to the scatter-estimation system 130 of FIG. 2) may generate a primary image 620 and a scatter image 630 based on the original image 610. Afterward, an image-correction module of the scatter-estimation system may perform a scale operation 635 to generate a gain map 640, and perform a scatter-reduction/scatter-correction operation 645 to generate a scatter-reduced image 650, based on the original image 610, the scatter image 630, and/or the gain map 640.

In some embodiments, the image-correction module may generate the scatter-reduced image 650 by directly subtracting the scatter image 630 from the original image 610 ("direct-subtraction approach"). Before performing the direct-subtraction, the image-correction module may first perform a scaling operation 635 to match the scatter image 630 to the original image 610 in terms of similar signal intensity. As the scatter image 630 may have its scatter signal normalized to one (1) source particle per Steradian (or "sr"), the image-correction module may compare the original image 610 with the scatter image 630 to determine a gain map 640 for each original image 610, and utilize this gain map 640 to scale the scatter image 630 accordingly. Afterward, the image-correction module may perform the scatter reduction/correction operation 650 by directly subtracting the scaled scatter image 630 from the original image 610, in order to generate the corresponding scatter-reduced image 470. Alternatively, the image-correction module may perform the scatter reduction/correction operation 650 by perturbation in order to generate the scatter-reduced image 470.

In some embodiments, the image-correction module may determine a gain map 640 for each original image 610 based on the following formula:

$$G(u',v')=M(u',v')/(A'_p(u',v')+A'_s(u',v')),$$

where the variable G denotes to the gain map; the variables (u', v') denotes to a corresponding pixel position in the images 610, 620 and 630; the variable M denotes to the original image 610; and the variables $A_p'$ and $A_s'$ denote to the primary image 620 and the scatter image 630, respective. The image-correction module may match the interpolation in projection angle for the primary image 620 and the scatter image 630 with the gantry angle of the original image 610.

In some embodiments, the image-correction module may generate a scatter-reduced image 660 based on a gain map 640 for each original image 610 using the following formula:

$$C(u,v)=M(u,v)-\tilde{G}(u,v)A'_s(u,v),$$

where the variable C denotes to the scatter-reduced image; the variables (u, v) denotes to a corresponding pixel position in the images 610, 620, and 630; the variable M denotes to the original image 610, the variables $A_s'$ denotes to the scatter image 630; and the variable G denotes to a smoothed version of the gain map 640. The image-correction module may smoothen the gain map 640 by applying a scatter fraction smoothing operation based on a maximum scatter fraction (e.g., SFmax=0.8).

In some embodiments, to scale the scatter image 630, the image-correction module may apply an image projection-dependent, spatially-varying gain map as described above, or apply a "projection-dependent scalar gain" or a "norm chamber based scalar gain." For example, the "projection-dependent scalar gain" could be the average (or median) of the gain map 640, or it could be the average value in a small region (e.g., 41×41 pixels) at the piercing point of the central ray (e.g., the smoothed gain map G(925,384) in half-fan geometry). The image-correction module may then apply this projection-dependent scalar gain to the entire calculated scatter image 630, before subtracting the scaled scatter image 630 from the measured image 610.

In some embodiments, the image-correction module may generate the scatter-reduced image 650 by performing a perturbation operation based on the scatter image 630 and the original image 610 ("perturbation approach"), especially when there may be imperfections in the object model and the virtual physics models used in the simulated CT scanning operation. In the perturbation approach, the image-correction module may generate a perturbation map by comparing the estimated primary image 620 with the original image 610. Afterward, the image-correction module may correct any errors in the original image 610 via the perturbation. The approach may eliminate the scaling issue with direct subtraction since the perturbation map is unitless.

Figure 7:
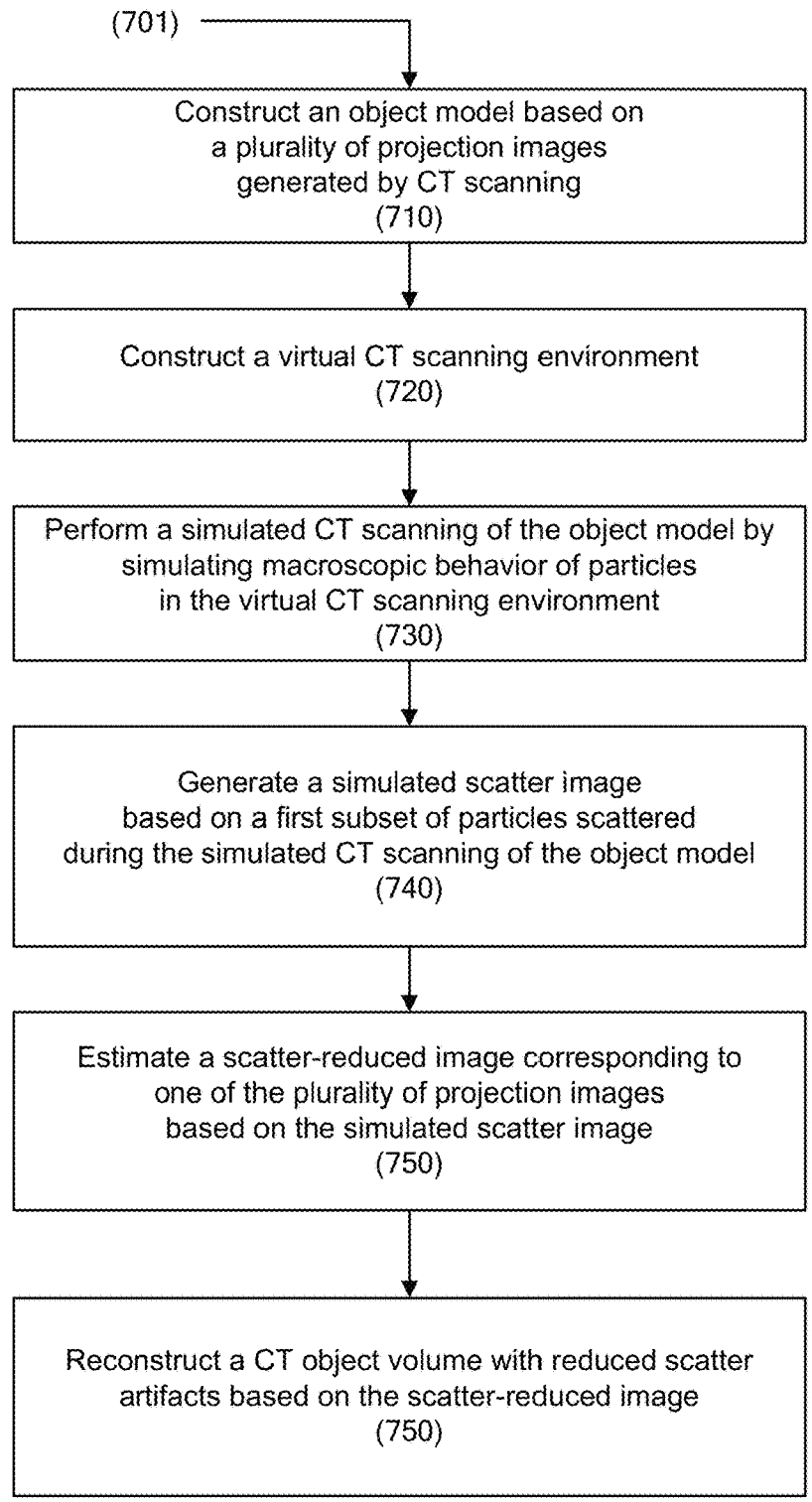
FIG. 7 shows a flow diagram illustrating one embodiment of a process to estimate scattered radiation contained in x-ray projections for CT reconstruction, all in accordance with certain embodiments of the present disclosure.

FIG. 7 shows a flow diagram illustrating one embodiment of a process 701 to estimate scattered radiation contained in x-ray projections for CT reconstruction, according to certain embodiments of the present disclosure. The process 701 sets forth various functional blocks or actions that may be described as processing steps, functional operations, events, and/or acts, which may be performed by hardware, software, and/or firmware. Those skilled in the art in light of the present disclosure will recognize that numerous alternatives to the functional blocks shown in FIG. 7 may be practiced in various implementations. In some embodiments, machine-executable instructions for the process 701 may be stored in memory, executed by a processing unit, and/or implemented in a scatter-estimation system, such as the scatter-estimation system 130 of FIG. 1.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments. Moreover, one or more of the outlined steps and operations may be performed in parallel.

At block 710, a scatter-estimation system may be configured to construct an object model based on a plurality of projection images generated by CT scanning of an object using an x-ray radiation source and a detector panel. The scatter-estimation system may construct a virtual patient table into the object model, and may extend the object model in its axial direction or longitudinal direction to account for truncation occurred during the CT scanning.

In some embodiments, the constructed object model may contain a plurality of voxels, and the scatter-estimation system may assign each of the plurality of voxels to a specific material type with density based on each of the plurality of voxels' Hounsfield Units (HU) value.

At block 720, the scatter-estimation system may be configured to construct a virtual CT scanning environment. Specifically, the constructing of the virtual CT scanning environment may include constructing a virtual radiation source for simulating the x-ray radiation source, and constructing a virtual detector panel for simulating the detector panel. In some embodiments, the x-ray radiation source has a Cone-beam CT (CBCT) geometry and the detector panel is a flat panel.

In some embodiments, the plurality of projection images may be generated using a bowtie filter, a collimator, and/or an anti-scatter grid. In these cases, the constructing of the virtual CT scanning environment may further include constructing a virtual bowtie filter based on the bowtie filter; constructing a virtual collimator based on the collimator; and/or constructing a virtual anti-scatter grid based on the anti-scatter grid.

At block 730, the scatter-estimation system may perform a simulated CT scanning of the object model by simulating macroscopic behavior of particles being emitted from the virtual radiation source, passing through the object model, and being detected by the virtual detector panel. In some embodiments, the scatter-estimation system may further simulate the macroscopic behavior of the particles passing through the virtual collimator and the virtual bowtie filter after being emitted from the virtual radiation source, as well as the virtual anti-scatter grid before being detected by the virtual detector panel.

In some embodiments, the scatter-estimation system may ray-trace the particles emitted from the virtual radiation source, passed through the plurality of voxels, and detected by a plurality of virtual pixels in the virtual detector panel, and identify the first subset of particles scattered during the ray-tracing. Specifically, the scatter-estimation system may perform the ray-tracing by transporting the particles emitted from the virtual radiation source through the plurality of voxels to calculate a set of scattering sources, transporting the particles from the set of scattering sources across the plurality of voxels, iterating through the calculation of scattering sources and transporting of the particles, and transporting the particles from the plurality of voxels to the plurality of pixels in the virtual detector panel.

At block 740, the scatter-estimation system may generate a simulated scatter image based on a first subset of particles scattered during the simulated CT scanning of the object model. Specifically, the scatter-estimation system may construct a Boltzmann Transport Equation (BTE) for the first subset of particles scattered, and use a deterministic method to solve the BTE and calculate the corresponding particle fluence distribution values in the plurality of voxels. Afterward, the scatter-estimation system may generate the simulated scatter image by ray-tracing the corresponding particle fluence distribution values of those voxels in the plurality of voxels that have the first subset of particles passing through before reaching the virtual pixels of the virtual detector panel.

In some embodiments, the spatial resolution of the plurality of pixels in the virtual detector panel is coarser than pixels in the detector panel. The scatter-estimation system may use interpolation to up-sample the simulated scatter image to match spatial resolution of one of the plurality of the projection images. Additionally, the scatter-estimation system may calculate a first subset of the plurality of simulated scatter images based on a subset of the plurality of projection images, and interpolate a second subset of the plurality of simulated scatter images based on the calculated first subset of the plurality of simulated scatter images. Typically, scatter images vary slowly over successive projections acquired in a CT scan, and simulating scatter images based on a subset of the plurality of projection images may allow for a reduction in the number of simulated scatter images. A second subset of the plurality of simulated scatter images may be rapidly computed by interpolation of the calculated first subset of the plurality of simulated scatter images.

In some embodiments, the plurality of pixels in the virtual detector panel may represent non-uniformly sampled points on the detector panel. The scatter-estimation system may use interpolation to up-sample the sampled points of the simulated scatter image to match spatial resolution of one of the plurality of the projection images. Additionally, the scatter-estimation system may calculate a first subset of the plurality of simulated scatter images based on a non-uniformly sampled subset of the plurality of projection images (e.g., higher sampling density when scatter is changing more rapidly between successive scatter images), and interpolate a second subset of the plurality of simulated scatter images based on the calculated first subset of the plurality of simulated scatter images.

In some embodiments, the scatter-estimation system may generate a simulated primary image based on a second subset of particles attenuated but not scattered during the simulated CT scanning of the object model, and generate a gain map based on the simulated primary image and the simulated scatter image. Afterward, the scatter-estimation system may estimate the scatter-reduced image by adjusting the plurality of projection images based on the simulated scatter image and the gain map. In some embodiments, the scatter-estimation system may estimate the scatter-reduced image by adjusting one of the plurality of projection images using subtraction or perturbation based on the simulated scatter image.

At block 750, the scatter-estimation system may estimate a scatter-reduced image corresponding to one of the plurality of projection images based on the simulated scatter image. At block 760, the scatter-estimation system may reconstruct a CT object volume with reduced scatter artifacts based on the scatter-reduced image.

Thus, methods and systems for estimating scattered radiation contained in x-ray projections have been described. The techniques introduced above can be implemented in special-purpose hardwired circuitry, in software and/or firmware in conjunction with programmable circuitry, or in a combination thereof. Special-purpose hardwired circuitry may be in the form of, for example, one or more application-specific integrated circuits (ASICs), programmable logic devices (PLDs), field-programmable gate arrays (FPGAs), and others.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. Those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

Software and/or firmware to implement the techniques introduced here may be stored on a non-transitory machine-readable storage medium and may be executed by one or more general-purpose or special-purpose programmable microprocessors. A "machine-readable storage medium", as the term is used herein, includes any mechanism that provides (i.e., stores and/or transmits) information in a form accessible by a machine (e.g., a computer, network device, personal digital assistant (PDA), mobile device, manufacturing tool, any device with a set of one or more processors, etc.). For example, a machine-accessible storage medium includes recordable/non-recordable media (e.g., read-only memory (ROM), random access memory (RAM), magnetic disk storage media, optical storage media, flash memory devices, etc.)

Although the present disclosure has been described with reference to specific exemplary embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense.

We claim:

1. A method to estimate scattered radiation contained in x-ray projections for computed tomography (CT) reconstruction, comprising:
    constructing an object model based on a plurality of projection images generated by CT scanning of an object using an x-ray radiation source and a detector panel, wherein the object model contains a plurality of voxels, and the constructing of the object model comprises assigning each of the plurality of voxels to at least one material type with density based on each of the plurality of voxels' Hounsfield Units (HU) value;
    constructing a virtual radiation source based on the x-ray radiation source;
    constructing a virtual detector panel based on the detector panel;
    performing a simulated CT scanning of the object model by simulating macroscopic behavior of particles being emitted from the virtual radiation source, passing through the object model, and being detected by the virtual detector panel;
    constructing a Boltzmann Transport Equation (BTE) for a first subset of particles scattered during the simulated CT scanning of the object model;
    using a deterministic method to solve the BTE and calculate the corresponding particle fluence distribution values in the plurality of voxels; and
    generating a simulated scatter image based on the corresponding particle fluence distribution values in the plurality of voxels.

2. The method as recited in claim 1, further comprising:
    estimating a scatter-reduced image corresponding to one of the plurality of projection images based on the simulated scatter image; and
    reconstructing a CT object volume with reduced scatter artifacts based on the scatter-reduced image.

3. The method as recited in claim 2, wherein the estimating of the scatter-reduced image comprising:
    generating a simulated primary image based on a second subset of particles attenuated but not scattered during the simulated CT scanning of the object model;
    generating a gain map based on the simulated primary image and the simulated scatter image; and
    estimating the scatter-reduced image by adjusting the plurality of projection images based on the simulated scatter image and the gain map.

4. The method as recited in claim 2, wherein the estimating of the scatter-reduced image comprising:
    estimating the scatter-reduced image by adjusting one of the plurality of projection images using subtraction or perturbation based on the simulated scatter image.

5. The method as recited in claim 1, wherein the plurality of projection images are generated using a bowtie filter, and the performing of the simulated CT scanning of the object model further comprising:
    constructing a virtual bowtie filter based on the bowtie filter; and
    simulating the macroscopic behavior of the particles passing through the virtual bowtie filter after being emitted from the virtual radiation source.

6. The method as recited in claim 1, wherein the plurality of projection images are generated using an anti-scatter grid, and the performing of the simulated CT scanning of the object model further comprising:
    constructing a virtual anti-scatter grid based on the anti-scatter grid; and
    simulating the macroscopic behavior of the particles passing through the virtual anti-scatter grid before being detected by the virtual detector panel.

7. The method as recited in claim 1, wherein the constructing of the object model comprising:
    constructing a virtual patient table into the object model.

8. The method as recited in claim 7, wherein the constructing of the object model further comprising:
    extending the object model in its axial direction or longitudinal direction to account for truncation occurred during the CT scanning.

9. The method as recited in claim 1, wherein the performing of the simulated CT scanning of the object model by simulating of the macroscopic behavior of particles comprising:
    simulating the particles emitted from the virtual radiation source, passed through the plurality of voxels, and detected by a plurality of virtual pixels in the virtual detector panel; and identifying the first subset of particles scattered during the simulating of the particles.

10. The method as recited in claim 9, wherein the simulating of the particles comprising:
transporting the particles emitted from the virtual radiation source through the plurality of voxels to calculate a set of scattering sources;
transporting the particles from the set of scattering sources across the plurality of voxels;
iterating through the calculation of scattering sources and transporting of the particles; and
transporting the particles from the plurality of voxels to the plurality of pixels in the virtual detector panel.

11. The method as recited in claim 1, further comprising:
ray-tracing the first subset of particles from the virtual radiation source to the object model prior to the constructing of the BTE; and
ray-tracing the first subset of particles from the object model to the virtual detector panel after the constructing of the BTE.

12. The method as recited in claim 1, wherein the spatial resolution of the plurality of pixels in the virtual detector panel is coarser than pixels in the detector panel, and the generating the simulated scatter image based on the corresponding particle fluence distribution values in the plurality of pixels further comprising:
using interpolation to up-sample the simulated scatter image to match spatial resolution of one of the plurality of the projection images.

13. A method to determine scattered radiation contained in x-ray projections for computed tomography (CT) reconstruction, comprising:
reconstructing a first CT volume based on a plurality of projection images generated by CT scanning of an object using an x-ray radiation source and a detector panel;
constructing an object model based on the CT volume, wherein the object model contains a plurality of voxels, and the constructing of the object model comprises assigning each of the plurality of voxels to at least one material type with density based on each of the plurality of voxels' Hounsfield Units (HU) value;
constructing a virtual CT scanning environment having a virtual radiation source based on the x-ray radiation source and having a virtual detector panel based on the detector panel, wherein the virtual detector panel contains a plurality of virtual pixels;
performing a simulated CT scanning of the object model by simulating macroscopic behavior of particles being emitted from the virtual radiation source, passing through the object model, and being detected by the virtual detector panel;
generating a plurality of simulated scatter images corresponding to the plurality of projection images by estimating a first subset of particles scattered during the simulated CT scanning of the object model, wherein each simulated scatter image in the plurality of simulated scatter images is generated by
constructing a Boltzmann Transport Equation (BTE) for the first subset of particles scattered during the simulated CT scanning of the object model,
using a deterministic method to solve the BTE and calculate corresponding particle fluence distribution values in the plurality of voxels, and
generating the simulated scatter image based on the corresponding particle fluence distribution values in the plurality of voxels; and
reconstructing a second CT volume with reduced scatter artifacts based on the plurality of projection images and the plurality of simulated scatter images.

14. The method as recited in claim 13, wherein a first subset of the plurality of simulated scatter images are calculated based on a subset of the plurality of projection images, and a second subset of the plurality of simulated scatter images are interpolated based on the calculated first subset of the plurality of simulated scatter images.

15. The method as recited in claim 13, wherein the x-ray radiation source has a Cone-beam CT (CBCT) geometry and the detector panel is a flat panel.

16. The method as recited in claim 13, wherein
generating the each simulated scatter image in the plurality of simulated scatter images further comprises:
ray-tracing the first subset of particles from the virtual radiation source to the object model prior to the constructing of the BTE.

17. The method as recited in claim 16, wherein generating the each simulated scatter image in the plurality of simulated scatter images further comprises:
ray-tracing the first subset of particles from the object model to the virtual detector panel after the constructing of the BTE.

18. A scatter-estimation system configured to estimate scattered radiation contained in x-ray projections for computed tomography (CT) reconstruction, comprising:
a scan-simulation module configured to
construct an object model based on a plurality of projection images generated by CT scanning of an object using an x-ray radiation source and a detector panel, wherein the object model contains a plurality of voxels, and the construction of the object model comprises assigning each of the plurality of voxels to at least one material type with density based on each of the plurality of voxels' Hounsfield Units (HU) value,
construct a virtual radiation source based on the x-ray radiation source,
construct a virtual detector panel based on the detector panel, and
perform a simulated CT scanning of the object model by simulating macroscopic behavior of particles being emitted from the virtual radiation source, passing through the object model, and being detected by the virtual detector panel; and
an image-correction module coupled with the scan-simulation module, wherein the image-correction module is configured to
generate a simulated scatter image by
constructing a Boltzmann Transport Equation (BTE) for a first subset of particles scattered during the simulated CT scanning of the object model,
using a deterministic method to solve the BTE and calculate corresponding particle fluence distribution values in the plurality of voxels, and
generating the simulated scatter image based on the corresponding particle fluence distribution values in the plurality of voxels, and
estimate a scatter-reduced image corresponding to one of the plurality of projection images based on the simulated scatter image.

19. The scatter-estimation system as recited in claim 18, wherein the plurality of projection images are generated using a bowtie filter and an anti-scatter grid, and the scan-simulation module is further configured to:

construct a virtual bowtie filter based on the bowtie filter;
construct a virtual anti-scatter grid based on the anti-scatter grid; and
simulating the macroscopic behavior of the particles passing through the virtual bowtie filter and the virtual anti-scatter grid before being detected by the virtual detector panel.

\* \* \* \* \*